US006953572B1

(12) United States Patent
Samain et al.

(10) Patent No.: US 6,953,572 B1
(45) Date of Patent: *Oct. 11, 2005

(54) COSMETIC COMPOSITIONS BASED ON PARTLY NEUTRALIZED ORGANIC SILICON COMPOUNDS

(75) Inventors: Henri Samain, Bièvres (FR); Isabelle Rollat, Boulogne-Billancourt (FR); Valérie Jeanne Rose, Paris (FR); Clément Sanchez, Gif-sur-Yvette (FR)

(73) Assignee: L'Oreal, (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/088,994

(22) PCT Filed: Sep. 27, 1999

(86) PCT No.: PCT/FR99/02289

§ 371 (c)(1),
(2), (4) Date: Jun. 27, 2002

(87) PCT Pub. No.: WO01/22925

PCT Pub. Date: Apr. 5, 2001

(51) Int. Cl.$^7$ .............................................. A61K 7/09
(52) U.S. Cl. .................. 424/70.12; 424/70.1; 424/401; 424/70.2
(58) Field of Search ........................... 424/70.12, 70.1, 424/70.2, 401

(56) References Cited

U.S. PATENT DOCUMENTS

| 3,914,416 A | 10/1975 | Gueyne et al. ............. 424/184 |
| 6,172,250 B1 | 1/2001 | Seguin et al. ............... 556/407 |

FOREIGN PATENT DOCUMENTS

| CH | 535 579 | 4/1973 |
| EP | 0 242 855 | 10/1987 |
| EP | 0 279 623 | 8/1988 |
| EP | 0 464 835 | 1/1992 |
| EP | 0 655 453 | 5/1995 |
| EP | 0 877 027 | 11/1998 |
| FR | 2 746 008 | 9/1997 |
| JP | 63-307811 | 12/1988 |
| WO | 79/00454 | 7/1979 |
| WO | 89/04163 | 5/1989 |

*Primary Examiner*—Jyothsna Venkat
(74) *Attorney, Agent, or Firm*—Steptoe & Johnson LLP

(57) ABSTRACT

The invention concerns a composition comprising in a cosmetically acceptable aqueous medium, at least 0.02 weight percent relative to the composition total weight, one or several water soluble organosilicon compounds, having one, two or three silicon atoms, at least a basic chemical function and at least two hydroxyl groups or groups capable of being hydrolyzed per molecule, said organosilicon compounds being partly neutralized with at least a neutralizing agent. The invention is applicable to hair care compositions.

11 Claims, No Drawings

COSMETIC COMPOSITIONS BASED ON PARTLY NEUTRALIZED ORGANIC SILICON COMPOUNDS

This application is a 371 of PCT/FR99/02289 filed on Oct. 27, 1999.

The present invention relates generally to aqueous cosmetic compositions, in particular for treating the hair, comprising unpolymerized or relatively unpolymerized, water-soluble organosilicon compounds.

It is common practice to use organic compounds such as polymers to prepare cosmetic compositions for treating the hair. For example, polymers are used that give, on drying, solid materials for fixing the hairstyle in a shape. Such materials are also used to give shape-holding effects. Polymer compounds, such as polysiloxanes, are also used to give haircare effects, particularly to damaged hair or hair that is difficult to disentangle. Cosmetic compositions containing these polymers are applied to the hair and left to dry or rinsed out before proceeding to dry.

The use of polymer compounds presents many drawbacks.

The first drawback lies in the fact that, when the polymers are used in compositions above a certain concentration, the compositions obtained are difficult to apply due to the increase in the viscosity of the compositions. This difficulty in applying the compositions leads to the hair being overloaded in certain areas and thus to cosmetic defects and also involves certain parts of the hair receiving less of the compositions, which, in the end, induces a reduced effect on these areas.

The second drawback lies in the fact that these compositions are occasionally difficult to use. Specifically, polymer compounds of low water solubility require the use of an organic solvent or a mixture of organic solvents. The use of an organic solvent entails several problems, for instance environmental problems and problems affecting the cosmetic quality of the hair.

To overcome these drawbacks, attention has thus turned toward the use of polymer compounds that have been made partially water-soluble. Thus, certain polymer compounds may be used in water without adding any co-solvent. In this case, the limitation lies in the fact that these polymer compounds are partially, or even totally, removed by rinsing the hair. Consequently, in this case, the effect due to the polymer compounds is very limited after rinsing. Ultimately, this limits the effect of rinse-out treatments (shampooing, conditioning), but also reduces the advantage of such compositions used in leave-in mode (hairsetting lotions, mousses, lacquers, etc.) since the user loses the effect acquired by the treatment when the user washes the hair.

Efforts have thus been devoted toward finding compounds for formulating cosmetic compositions that can be used in water and that retain their effect when the hair is rinsed.

Thus, U.S. Pat. No. 4,344,763 (Gillette) describes cosmetic compositions comprising an organosiloxane monomer such as an aminoalkylalkoxysilane and an organic titanate dissolved in an alcohol.

More specifically, the patent describes a process for shaping the hair which consists in moistening the hair with water and then in applying a solution containing, in isopropanol, from 0.5% to 15% by weight of an aminoalkylalkoxysilane and from 0.005% to 1.5% by weight of an organic titanate, and then in placing the hair in the desired shape.

According to this process, it is particularly recommended to keep the isopropanol solution protected from any moisture.

A process has also been disclosed, in EP 113 992, for simultaneously fixing and conditioning the hair using a composition that is stable in the absence of moisture, containing (A) a siloxane oligomer containing at least one nitrogen-hydrogen bond, and (B) an anhydrous, readily hydrolyzable additive chosen from titanates, zirconates, vanadates, germanates, and mixtures thereof.

The solvent for the composition is an aliphatic hydrocarbon or an aliphatic halohydrocarbon, preferably 1,1,1-trichloroethane.

After applying the composition to the hair, the hair is placed in a humid atmosphere so as to bring about the crosslinking of the siloxane oligomer and of the readily hydrolyzable anhydrous additive.

There is thus a need for a stable cosmetic composition, in particular for treating the hair, which is essentially aqueous and which makes it possible to obtain a sufficient cosmetic effect, in particular for the hair, in rinse-out or leave-in mode.

One subject of the present invention is thus stable, aqueous cosmetic compositions, in particular cosmetic compositions for hair treatment and haircare, which overcome the drawbacks of the prior art.

More specifically, one subject of the present invention is stable, aqueous cosmetic compositions for hair treatment and haircare, which give the hair a long-lasting styling effect and a pleasant feel.

The inventors have found, surprisingly, that it is possible to formulate cosmetic compositions not requiring the use of an organic solvent and having an effective, rinse-fast cosmetic effect, without the risk of problems of the hair being charged in the event of overloading, by using in these compositions unpolymerized or relatively unpolymerized, water-soluble organosilicon compounds comprising at least one basic and partially neutralized chemical function.

It has been observed that when such compositions are applied, pronounced cosmetic effects are obtained without any problems in the event of overloading, and the effects of which are very rinse-fast and wash-fast.

According to the invention, the cosmetic compositions, in particular for treating the hair, comprise, in a cosmetically acceptable aqueous medium, at least 0.02% by weight, relative to the total weight of the composition, of one or more unpolymerized or relatively unpolymerized, water-soluble organosilicon compounds chosen from organosilanes comprising one silicon atom and organosiloxanes comprising two or three silicon atoms, the organosilicon compounds also comprising at least one basic chemical function and at least two hydrolyzable or hydroxyl groups per molecule, characterized in that the compositions comprise an amount of a neutralizing agent such that the unpolymerized or relatively unpolymerized organosilicon compounds are neutralized to a proportion of from 1/1000 to 99/100 and preferably from 0.2/100 to 70/100.

The organosilicon compounds according to the invention are capable of forming, in aqueous medium, a nonhybrid compound, after self-condensation and evaporation of the support. The expression "nonhybrid compound" means a compound that is chemically homogeneous as regards silicon, that is to say that it contains no other additional metallic or organometallic species.

The unpolymerized or relatively unpolymerized organosilicon compounds that are useful in the compositions of the present invention are chosen from water-soluble organosilanes comprising one silicon atom and water-soluble organosiloxanes comprising two or three silicon atoms, preferably two silicon atoms. They must also comprise at least one basic chemical function, and preferably only one basic chemical function. The basic chemical function may be any function that gives the silicon compound a basic nature without harming its solubility in water and is preferably an amine function such as a primary, secondary or tertiary amine function. The basic chemical function of the silicon compounds according to the invention may optionally comprise other functions such as, for example, another amine function, an acid function or a halogen function.

The organosilicon compounds that are useful in the compositions of the present invention also comprise at least two hydrolyzable or hydroxyl groups per silicon atom. The hydrolyzable groups are preferably alkoxy, aryloxy or halogen groups. They may also optionally comprise other chemical functions such as acid or amine functions.

The organosilanes that are preferred according to the invention correspond to the formula:

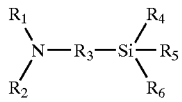

in which:

$R_4$ represents a halogen or an OR' or $R'_1$ group;

$R_5$ represents a halogen or an OR" or $R'_2$ group;

$R_6$ represents a halogen or an OR''' or $R'_3$ group;

and $R_1$, $R_2$, $R_3$, R', R", R''', $R'_1$, $R'_2$ and $R'_3$ represent, independently of each other, a saturated or unsaturated, linear or branched hydrocarbon-based group optionally bearing additional chemical groups such as acid or amine groups, $R_1$, $R_2$, R', R" and R''' also possibly denoting hydrogen, and at least two of the groups $R_4$, $R_5$ and $R_6$ being other than the groups $R'_1$, $R'_2$ and $R'_3$.

Preferably, $R_1$, $R_2$, R', R" and R''', $R'_1$, $R'_2$ and $R'_3$ represent a $C_1$ to $C_{12}$ alkyl group, a $C_6$ to $C_{14}$ aryl group, a ($C_1$ to $C_8$)alkyl ($C_6$ to $C_{14}$)aryl group or a ($C_6$ to $C_{14}$)aryl($C_1$ to $C_8$)alkyl group; and $R_3$ is preferably a $C_1$ to $C_{12}$ alkyl group, a $C_6$ to $C_{14}$ aryl group, a ($C_1$ to $C_8$)alkyl ($C_6$ to $C_{14}$)aryl group or a ($C_6$ to $C_{14}$)aryl ($C_1$ to $C_8$)alkyl group.

The organosiloxanes that are preferred in the compositions of the present invention may be represented by the formula:

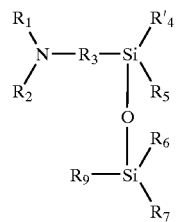

in which:

$R_1$, $R_2$, $R_3$, $R_5$ and $R_6$ are defined as above;

$R'_4$ represents a halogen or an $OR_{11}$ group;

$R_7$ represents a halogen or an $OR_{10}$ or $R''_1$ group $R_9$ represents a halogen or an $OR_8$, $R''_2$ or $R_3NR_1R_2$ group;

$R''_1$, $R''_2$, $R_8$, $R_{10}$ and $R_{11}$ represent a saturated or unsaturated, linear or branched hydrocarbon-based group optionally bearing additional chemical groups such as basic solubilizing groups;

$R_{11}$, $R_{10}$ and $R_8$ also possibly denoting hydrogen.

Preferably, $R''_1$, $R''_2$, $R_8$ or $R_{10}$ and $R_{11}$ represent a $C_1$ to $C_{12}$ alkyl group, a $C_6$ to $C_{14}$ aryl group, a ($C_1$ to $C_8$)alkyl($C_6$ to $C_{14}$)aryl group and a ($C_6$ to $C_{14}$)aryl($C_1$ to $C_8$)alkyl group.

At least one of the groups $R_6$, $R_7$ and $R_9$ denotes a halogen or a group OR''', $OR_{10}$ or $OR_8$.

Preferably, the halogen is chlorine.

One important aspect of the compositions of the invention is that the unpolymerized or relatively unpolymerized organosilicon compounds are partially neutralized using a neutralizing agent or pH regulator, such that the neutralization reaches 1/1000 to 99/100 and better still from 0.2/100 to 70/100. More preferably, the neutralization is from 0.2/100 to 60/100.

The pH regulators may be any cosmetically acceptable acids or mixtures of acids. Among the acids that may be used, mention may be made of hydrochloric acid, nitric acid and mono-, di- or tricarboxylic organic acids.

This partial neutralization of the unpolymerized or relatively unpolymerized organosilicon compounds of the compositions of the invention represents an important aspect for the production of the desired properties for the compositions.

Another important aspect of the compositions according to the invention is that the organosilicon compounds, the pH regulators and also the other constituents of the composition are chosen such that this composition contains large amounts of the unpolymerized or relatively unpolymerized organosilicon compounds, that is to say compounds comprising one, two or three silicon atoms. Thus, it is necessary for the composition to contain, relative to the total weight of the composition, at least 0.02% of unpolymerized or relatively unpolymerized organosilicon compounds and preferably at least 0.5% by weight, possibly ranging up to 50% by weight.

The content of unpolymerized or relatively unpolymerized organosilicon compounds according to the invention is determined by the usual analysis methods such as silicon-29 and proton NMR spectroscopy, and by chromatography.

The compositions according to the invention are aqueous compositions. However, it is possible, for example for the use of adjuvants, to add a cosolvent such as an alcohol or a ketone, for example ethanol or acetone.

In a known manner, all the compositions of the invention may contain adjuvants commonly used in cosmetics, such as oils, waxes or other common fatty substances; standard gelling agents and/or thickeners; emulsifiers; moisturizers; emollients; sunscreens; hydrophilic or lipophilic active agents, for instance ceramides; free-radical scavengers; surfactants; polymers; proteins; bactericides; sequestering agents; antidandruff agents; antioxidants; preserving agents; fragrances; fillers; dyestuffs.

The amounts of these various adjuvants are those conventionally used in the field under consideration.

Needless to say, a person skilled in the art will take care to select the optional compound(s) added to the composition according to the invention such that the advantageous properties intrinsically associated with the composition in accordance with the invention are not, or are not substantially, adversely affected by the envisaged addition.

The compositions according to the invention may be used in rinse-out or leave-in mode.

The compositions according to the invention may be in any form that is suitable for topical application, especially in the form of solutions of the lotion or serum type; in the form of aqueous gels; in the form of emulsions obtained by dispersing a fatty phase in an aqueous phase (O/W) or, conversely, (W/O), of more or less thick liquid consistency such as more or less unctuous milks and creams.

These compositions are prepared according to the usual methods.

The compositions according to the invention are preferably used as hair products, especially for holding the hairstyle or for shaping the hair. They may also give the hair a temporary coloration or provide the hair with good protection against the effects of UV radiation, while at the same time providing hair holding or fixing properties.

The hair compositions according to the invention are preferably styling products such as hairsetting gels or lotions, blow-drying lotions, and fixing and styling compositions such as lacquers or sprays.

The lotions may be packaged in various forms, especially in vaporizers, in pump-dispenser bottles or in aerosol containers to allow an application of the composition in vaporized form or in the form of a mousse. Such packaging forms are indicated, for example, when it is desired to obtain a spray or mousse for fixing or treating the hair.

A subject of the present invention is also the use of the composition according to the invention in a process for treating the hair, in order to hold and/or color it.

According to one embodiment of this process, the composition is applied to rinsed or unrinsed hair, preferably in the form of a spray, either using a pump-dispenser bottle or using an aerosol.

After spraying onto the head of hair, the composition is left to act and to dry.

The hair may be rinsed after applying the composition.

The hair may be placed in the desired shape, either before the application or immediately after.

The drying time may be variable and depends on the nature of the composition.

After combing, the hair has a very pleasant feel quality.

The invention is illustrated by the examples that follow.

EXAMPLE 1

The four formulations below were prepared:

| Compositions | Water-soluble unpolymerized or relatively unpolymerized silicon compound Aminopropyltriethoxysilane (g per 100 g of composition) | Neutralizing agent Hydrochloric acid (amount of neutralization (normality) relative to the amount of soluble silane) | Water |
|---|---|---|---|
| 1 | 12 g | 0 | qs 100 g |
| 2 | 12 g | 0.5 | qs 100 g |
| 3 | 12 g | 0.25 | qs 100 g |
| 4 | 12 g | 0.75 | qs 100 g |

The silicon-29 NMR analysis shows that these two compositions contain about 10 g of organosilicon compounds containing one, two or three silicon atoms per 100 g of composition (NMR peaks present at a chemical shift ranging from −30 to −75 ppm (tetramethylsilane being used as reference)).

The four compositions are used in the following applications:

Application 1: Leave-in Application. Production of a Styling Effect.

The compositions are introduced into an aerosol can in a proportion of 65 g. The aerosol can is fitted with a 51 P valve and a $CO_2$ 045 diffuser. 35 g of dimethyl ether are added to each can.

Two locks of 5 g of natural hair are prepared. The hairs are held at the roots by a clip and are arranged in a triangle.

Compositions 1, 2 and 3 are sprayed onto the locks for 5 seconds per face. After drying (15 minutes), a panel of 8 trained testers evaluates the styling effect, on a scale from 0 to 50; 0 corresponds to no styling effect and 50 to a very strong styling effect.

A disentangling is performed and a panel of 8 trained testers evaluates the feel qualities of the locks thus treated.

The feel quality is graded on a scale from 0 to 50; 0 corresponds to a very poor feel quality and 50 to a very pleasant feel quality.

The grades from the 8 testers are totalled for each composition and the average is then determined.

The following results are obtained:

| Compositions | Average of the "styling effect" grades | Average of the "feel quality after disentangling" grades |
|---|---|---|
| 1 | 10 | 15 |
| 2 | 30 | 20 |
| 3 | 30 | 15 |

The results show that with the partially neutralized compositions, a better styling effect and a feel quality after disentangling that is at least equal to that of a non-neutralized composition are obtained.

Application 2: Leave-in Application. Production of a Styling Effect.

Two locks of 5 g of natural hair are prepared. The hairs are held at the roots and left free over the remainder of the length.

The compositions are placed in contact with the locks for 2 minutes (the locks are immersed in 10 ml of the test solution). They are then left to dry for 24 hours.

After drying, the hairs are stuck together in all cases.

A disentangling is performed and a panel of 8 trained testers evaluates the feel qualities of the locks thus treated.

The feel quality is graded on a scale from 0 to 50; 0 corresponds to a very poor feel quality and 50 to a very pleasant feel quality.

The grades from the 8 testers are totalled for each composition and the average is then determined.

The table summarizes the results:

| Compositions | Average of the "feel quality after disentangling" grades |
|---|---|
| 1 | 10 |
| 2 | 25 |
| 3 | 25 |
| 4 | 15 |

The results show that with the partially neutralized compositions according to the invention a better feel quality after disentangling is obtained, in leave-in application, compared with a non-neutralized composition.

What is claimed is:

1. A cosmetic composition comprising, in a cosmetically acceptable aqueous medium, at least 0.02% by weight, relative to the total weight of the composition, of at least one substantially unpolymerized water-soluble organosilicon compound, the organosilicon compound being:

a silane having one silicon atom having the formula:

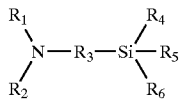

in which:

$R_4$ represents a halogen or an OR' or $R'_1$ group:
$R_5$ represents a halogen or an OR" or $R'_2$ group;
$R_6$ represents a halogen or an OR''' or $R'_3$ group;
$R_1$, $R_2$, $R_3$, R', R", R''', $R'_1$, $R'_2$ and $R'_3$ represent, independently of each other, an acid substituted or unsubstituted, saturated or unsaturated, linear or branched hydrocarbon-based group,
$R_1$, $R_2$, R', R" and R''' may represent, independently of each other, hydrogen, at least two of the groups $R_4$ $R_5$ and $R_6$ being other than the groups $R'_1$, $R'_2$ and $R'_3$, or a siloxane having two or three silicon atoms, the organosilicon compound having at least one basic chemical function and at least two hydrolyzable or hydroxyl groups per molecule, the composition containing a sufficient amount of a neutralizing agent such that the organosilicon compound is neutralized to a proportion of from 1/1000 to 99/100.

2. The cosmetic composition of claim 1, wherein the organosilicon compound represents at least 0.5% and up to 50% by weight of the composition.

3. The composition of claim 1, wherein the basic chemical function of the organosilicon compound is a primary, secondary or tertiary amine.

4. The composition of claim 1, wherein the hydrolyzable groups are alkoxy, aryloxy or halogen groups.

5. The composition of claim 1, wherein the neutralizing agent is an acid.

6. The composition of claim 5, wherein the neutralizing agent is hydrochloric acid, nitric acid or a mono-, di- or tricarboxylic organic acid.

7. The composition of claim 1, wherein the composition is in the form of a hair product.

8. The composition of claim 7, wherein the composition is in the form of a hair product for holding the hair or for shaping the hair.

9. The composition of claim 1, wherein the organosilicon compound is neutralized to a proportion of from 0.2/100 to 70/100.

10. The cosmetic composition of claim 1, wherein the organosilicon compound has the formula:

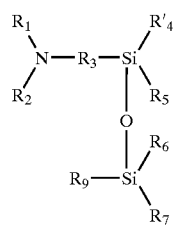

in which:

$R'_4$ represents a halogen or an $OR_{11}$ group;
$R_5$ represents a halogen or an OR" or $R'_2$ group;
$R_6$ represents a halogen or an OR''' or $R'_3$ group;
$R_7$ represents a halogen or an $OR_{10}$ or $R''_1$ group;
$R_9$ represents a halogen or an $OR_8$, $R''_2$ or $R_3NR_1R_2$ group;
$R_1$, $R_2$, $R_3$, R", R''', $R'_2$ and $R'_3$ represent, independently of each other, a substituted or unsubstituted, saturated or unsaturated, linear or branched hydrocarbon-based group;
$R_1$, $R_2$, R" and R''' may represent, independently of each other, hydrogen, at least two of the groups $R_5$ and $R_6$ being other than the groups $R'_2$ and $R'_3$;
$R''_1$, $R''_2$, $R_8$, $R_{10}$ and $R_{11}$ represent a substituted or unsubstituted, saturated or unsaturated, linear or branched hydrocarbon-based group; and
$R_{11}$, $R_{10}$ and $R_8$ may represent, independently of each other, hydrogen, at least one of the groups $R_6$, $R_7$ and $R_9$ denoting a halogen or an OR''', $OR_{10}$ or $OR_8$ group.

11. The cosmetic composition of claim 10, wherein the groups $R_1$, $R_2$, R', $R'_1$, $R'_2$, $R'_3$, R", R''', $R''_1$, $R''_2$, $R_8$, $R_{10}$ and $R_{11}$ are a $C_1$ to $C_{12}$ alkyl radical, a $C_6$ to $C_{14}$ aryl radical, a ($C_1$ to $C_8$)alkyl($C_6$ to $C_{14}$)aryl radical or ($C_6$ to $C_{14}$)aryl($C_1$ to $C_8$)alkyl radical.

* * * * *